US 12,322,197 B2

(12) United States Patent
Lemay et al.

(10) Patent No.: US 12,322,197 B2
(45) Date of Patent: *Jun. 3, 2025

(54) INTELLIGENT IMAGE SEGMENTATION PRIOR TO OPTICAL CHARACTER RECOGNITION (OCR)

(71) Applicant: ABIOMED, Inc., Danvers, MA (US)

(72) Inventors: Paul Roland Lemay, Danvers, MA (US); Alessandro Simone Agnello, Danvers, MA (US)

(73) Assignee: ABIOMED, INC., Danvers, MA (US)

(*) Notice: Subject to any disclaimer, the term of this patent is extended or adjusted under 35 U.S.C. 154(b) by 71 days.

This patent is subject to a terminal disclaimer.

(21) Appl. No.: 18/099,294

(22) Filed: Jan. 20, 2023

(65) Prior Publication Data

US 2023/0230405 A1 Jul. 20, 2023

Related U.S. Application Data

(63) Continuation of application No. 17/036,793, filed on Sep. 29, 2020, now Pat. No. 11,587,337, which is a
(Continued)

(51) Int. Cl.
*G06V 30/40* (2022.01)
*G06F 18/21* (2023.01)
(Continued)

(52) U.S. Cl.
CPC .......... *G06V 30/40* (2022.01); *G06F 18/2163* (2023.01); *G06F 18/22* (2023.01);
(Continued)

(58) Field of Classification Search
CPC ...... G06T 3/4038; G16H 30/40; G16H 40/60; G06V 20/62; G06V 30/10; G06V 30/40;
(Continued)

(56) References Cited

U.S. PATENT DOCUMENTS 8,885,951 B1 11/2014 Cristofano et al.
8,897,598 B1 11/2014 Ziegler et al.
(Continued)

FOREIGN PATENT DOCUMENTS

| CN | 106027664 A | 10/2016 |
|---|---|---|
| JP | H08212269 A | 8/1996 |
| JP | 2014241089 A | 12/2014 |

OTHER PUBLICATIONS

Office Action issued in corresponding Japanese Patent Application No. 2021-556404, mailed Apr. 24, 2024, 6 pages.
(Continued)

*Primary Examiner* — Katrina R Fujita
(74) *Attorney, Agent, or Firm* — Botos Churchill IP Law LLC

(57) ABSTRACT

A medical device monitoring system and method extract information from screen images from medical device controllers, with a single OCR process invocation per screen image, despite critical information appearing in different screen locations, depending on which medical device controller's screen image is processed. For example, different software versions of the medical device controllers might display the same type of information in different screen locations. Copies of the critical screen information, one copy from each different screen location, are made in a mosaic image, and then the mosaic image is OCR processed to produce text results. Text is selectively extracted from the OCR text results, depending on contents of a selector field on the screen image, such as a software version number or a heart pump model identifier.

20 Claims, 10 Drawing Sheets

Related U.S. Application Data continuation of application No. 16/360,270, filed on Mar. 21, 2019, now Pat. No. 10,824,898.

(51) Int. Cl.
| | |
|---|---|
| *G06F 18/22* | (2023.01) |
| *G06T 3/4038* | (2024.01) |
| *G06V 20/62* | (2022.01) |
| *G06V 30/10* | (2022.01) |
| *G16H 30/40* | (2018.01) |
| *G16H 40/60* | (2018.01) |

(52) U.S. Cl.
CPC ............ *G06T 3/4038* (2013.01); *G06V 20/62* (2022.01); *G16H 30/40* (2018.01); *G16H 40/60* (2018.01); *G06V 30/10* (2022.01); *G06V 2201/02* (2022.01)

(58) Field of Classification Search
CPC .. G06V 2201/02; G06F 18/2163; G06F 18/22
See application file for complete search history.

(56) References Cited

U.S. PATENT DOCUMENTS

| | | |
|---|---|---|
| 2011/0150336 A1 | 6/2011 | Van |
| 2012/0330680 A1 | 12/2012 | O'Larte |
| 2014/0098209 A1 | 4/2014 | Neff |
| 2015/0100333 A1 | 4/2015 | Fitzgerald et al. |
| 2018/0107792 A1 | 4/2018 | Rajan et al. |
| 2018/0374568 A1 | 12/2018 | Agnello |
| 2019/0089533 A1 | 3/2019 | Agnello |
| 2019/0290215 A1 | 9/2019 | Gilbert |
| 2020/0098473 A1 | 3/2020 | Agnello et al. |

OTHER PUBLICATIONS

Office Action from corresponding Indian Patent Application No. 202117044529 dated Sep. 12, 2023 (10 pp.).

International Searching Authority—International Search Report International Application No. PCT/US20/23899 dated Jul. 7, 2020, together with the Written Opinion of the International Searching Authority, 8 pages.

Office Action from corresponding Australian Patent Application No. 2020240311 dated Nov. 28, 2024 (2 pp.).

INTELLIGENT IMAGE SEGMENTATION PRIOR TO OPTICAL CHARACTER RECOGNITION (OCR)

CROSS-REFERENCE TO RELATED APPLICATIONS

This application is a continuation of U.S. patent application Ser. No. 17/036,793, filed on Sep. 29, 2020, now U.S. Pat. No. 11,587,337, which application is a continuation of U.S. patent application Ser. No. 16/360,270, filed on Mar. 21, 2019, now U.S. Pat. No. 10,824,898, the disclosures of which are incorporated herein by reference.

TECHNICAL FIELD

The present invention relates to remotely monitoring medical devices and, more particularly, to intelligently segmenting an image of a screen displayed by a medical device controller prior to optical character recognition (OCR) processing the image.

BACKGROUND

Many medical devices, such as some intravascular blood pumps, for example the Impella® 2.5 heart pump available from Abiomed, Inc., Danvers, MA, are connected to external medical device controllers that collect and display operational data about the medical devices, such as heart signal level, battery temperature, blood flow rate and plumbing integrity. An exemplary medical device controller is available from Abiomed, Inc. under the trade name Automated Impella Controller®. The medical device controllers raise alarms when operational data values fall beyond predetermined values or ranges, for example if a leak or loss of suction is detected. These medical device controllers include video display screens as human interfaces, on which the operational data and/or alarms are displayed.

To facilitate remote monitoring by medical personnel to ensure efficacy and patient safety, some such medical device controllers may be coupled via computer networks, often including wireless segments, to central servers, which may be accessed by monitoring stations. The monitoring stations may display real-time operational data and/or alarms on display screens for viewing by the medical personnel.

The servers request and receive images of contents displayed on the screens of the medical device controllers. Some servers use optical character recognition (OCR) technology to parse the images and extract textual information, such as heart pump serial number, blood flow rate, warning message text and the like. To reduce OCR errors, some servers mask portions of the screen images that contain irrelevant text or graphics that might confuse an OCR engine.

However, different medical device controllers might display the same kind of information, for example blood flow rate, at different locations on their respective screens, for example depending on which version of software the medical device controllers execute, or depending on which type of heart pump is connected to the medical device controller. This ambiguity in screen location makes it difficult or impossible to effectively mask appropriate portions of the screen images prior to OCR. Consequently, the servers may use several masks and perform an OCR process with each mask, and then choose one OCR result. However, OCR processing is costly and time-consuming. Providers would prefer to have the servers perform only one OCR process per screen image. Unfortunately, the servers are not clairvoyant and cannot, therefore, determine ahead of time which mask to use.

BRIEF SUMMARY

An embodiment of the present invention provides a medical device monitoring system. The system includes a server. The server is configured to automatically request and receive "received images." The server is configured to request and receive the received images via a computer network. The server is configured to request and receive the received images from each medical device controller of a plurality of medical device controllers. Each received image contains contents displayed on a screen of a medical device controller. The plurality of medical device controllers includes a plurality of first medical device controllers and a plurality of second medical device controllers. For example, the first medical device controllers may execute software of a particular version, and the second medical device controllers may execute software of a different version. In another example, different types of medical devices are connected, respectively, to the first and second medical device controllers.

Each first medical device controller is configured to display information of a first type at first screen coordinates. Each second medical device controller is configured to display information of the first type at second screen coordinates, different from the first screen coordinates. In other words, the first and second medical device controllers display some information, such as a minimum blood flow rate, (the "first information") in different locations on their respective screens. This difference in screen locations may be due to the difference in software version or due to the different types of medical devices connected to the first and second medical device controllers.

For each received image, the server is configured to automatically generate a mosaic image. In order to generate the mosaic image, the server is configured to copy a first source region of the received image to a predefined destination region at third coordinates in the mosaic image. The first source region encompasses the first screen coordinates of the received image. The server is also configured to copy a second source region of the received image to a predefined destination region at fourth coordinates in the mosaic image. The fourth coordinates are different from the third coordinates. The second source region encompasses the second screen coordinates of the received image. The server is further configured to copy a plurality of additional source regions of the received image to respective additional predefined destination regions in the mosaic image.

After the mosaic image is generated, the server is configured to automatically have the mosaic image optical-character-recognized in a single service call to produce text results.

The server is also configured to automatically extract a selector text result from the text results. The selector text result corresponds to at least one of the additional predefined destination regions in the mosaic image. The server is configured to compare the selector text result to first predefined text. If the selector text result is found to match the first predefined text, the server is configured to extract a selected text result from the text results, such that the selected text result corresponds to the third coordinates in the mosaic image. Otherwise, the server is configured to extract the selected text result from the text results, such that the selected text result corresponds to the fourth coordinates in the mosaic image. The server is configured to provide the selected text result.

Thus, although the medical device controllers may display the same information in different screen locations, the server is able to select OCR results from an appropriate one of the screen locations, based on contents of another field on the screen, without having to perform two OCR processes.

In any embodiment, the server may be configured, if the selector text result is found to not match the first predefined text, to automatically compare the selector text result to second predefined text. The second predefined text is different from the first predefined text. If the selector text result is found to match the second predefined text, the server may be configured to automatically extract the selected text result from the text results, such that the selected text result corresponds to the fourth coordinates in the mosaic image.

In any embodiment, the at least one of the additional predefined destination regions in the mosaic image may correspond to an additional source region that contains a version number of software executed by the medical device controller.

In any embodiment, the at least one of the additional predefined destination regions in the mosaic image may correspond to an additional source region that contains an identifier of a medical device coupled to the medical device controller.

In any embodiment, the identifier of the medical device may include a serial number.

In any embodiment, the identifier of the medical device may include a type code.

In any embodiment, the at least one of the additional predefined destination regions in the mosaic image may correspond to an additional source region that contains an identifier of an optional feature installed on the medical device controller.

In any embodiment, the predefined destination region at the third coordinates in the mosaic image may be larger than the first source region. To copy the first source region to the predefined destination region at the third coordinates, the server may be configured to magnify the first source region so as to fill the predefined destination region at the third coordinates.

In any embodiment, to copy the first source region to the predefined destination region at the third coordinates, the server may be configured to convert each colored pixel of the first source region to a white pixel in the predefined destination region at the third coordinates.

Another embodiment of the present invention provides a method of monitoring a medical device. The method includes requesting and receiving received images. The requested images are requested and received via a computer network. The received images are requested and received from each medical device controller of a plurality of medical device controllers. Each received images includes contents displayed on a screen of the medical device controller. The plurality of medical device controllers includes a plurality of first medical device controllers and a plurality of second medical device controllers. Each first medical device controller is configured to display information of a first type at first screen coordinates, and each second medical device controller is configured to display information of the first type at second screen coordinates, different from the first screen coordinates.

For each received image, the method includes generating a mosaic image. Generating the mosaic image includes coping a first source region, which encompasses the first screen coordinates of the received image, to a predefined destination region at third coordinates in the mosaic image. A second source region, which encompasses the second screen coordinates of the received image, is copied to a predefined destination region at fourth coordinates, different from the third coordinates, in the mosaic image. A plurality of additional source regions of the received image is copied to respective additional predefined destination regions in the mosaic image.

After generating the mosaic image, the mosaic image is optical-character-recognized in a single service call to produce text results. A selector text result is extracted from the text results. The selector text result corresponds to at least one of the additional predefined destination regions in the mosaic image. The selector text result is compared to first predefined text.

If the selector text result is found to match the first predefined text, a selected text result is extracted from the text results, such that the selected text result corresponds to the third coordinates in the mosaic image. Otherwise, the selected text result is extracted from the text results, such that the selected text result corresponds to the fourth coordinates in the mosaic image. The selected text result is then provided.

In any embodiment, otherwise extracting the selected text result may include comparing the selector text result to second predefined text. The second predefined text may be different from the first predefined text. If the selector text result is found to match the second predefined text, the selected text result may be extracted from the text results, such that the selected text result corresponds to the fourth coordinates in the mosaic image.

In any embodiment, the at least one of the additional predefined destination regions in the mosaic image may correspond to an additional source region that contains a version number of software executed by the medical device controller.

In any embodiment, the at least one of the additional predefined destination regions in the mosaic image may correspond to an additional source region that contains an identifier of a medical device coupled to the medical device controller.

In any embodiment, the identifier of the medical device may include a serial number.

In any embodiment, the identifier of the medical device may include a type code.

In any embodiment, the at least one of the additional predefined destination regions in the mosaic image may correspond to an additional source region that contains an identifier of an optional feature installed on the medical device controller.

In any embodiment, the predefined destination region at the third coordinates in the mosaic image may be larger than the first source region. Copying the first source region to the predefined destination region at the third coordinates may include magnifying the first source region so as to fill the predefined destination region at the third coordinates.

In any embodiment, copying the first source region to the predefined destination region at the third coordinates may include converting each colored pixel of the first source region to a white pixel in the predefined destination region at the third coordinates.

Yet another embodiment of the present invention provides a non-transitory computer-readable medium encoded with instructions. When executed by a processor, the instructions establish processes for performing a computer-implemented method of monitoring a medical device. The processes include a process configured to request and receive, via a computer network, from each medical device controller of a plurality of medical device controllers, received images of contents displayed on a screen of the medical device controller. The plurality of medical device controllers includes a plurality of first medical device controllers, each configured to display information of a first type at first screen coordinates, and a plurality of second medical device controllers, each configured to display information of the first type at second screen coordinates, different from the first screen coordinates.

The processes also include a process configured to, for each received image, generate a mosaic image. The process is configured to copy a first source region, which encompasses the first screen coordinates of the received image, to a predefined destination region at third coordinates in the mosaic image. The process is also configured to copy a second source region, which encompasses the second screen coordinates of the received image, to a predefined destination region at fourth coordinates, different from the third coordinates, in the mosaic image. The process is further configured to copy a plurality of additional source regions of the received image to respective additional predefined destination regions in the mosaic image.

The processes further include a process configured to, after generating the mosaic image, have the mosaic image optical-character-recognized in a single service call to produce text results.

The processes include a process configured to extract a selector text result from the text results. The selector text result corresponds to at least one of the additional predefined destination regions in the mosaic image. The processes include a process configured to compare the selector text result to first predefined text.

The processes include a process configured to, if the selector text result is found to match the first predefined text, extract a selected text result from the text results, such that the selected text result corresponds to the third coordinates in the mosaic image, otherwise extract the selected text result from the text results, such that the selected text result corresponds to the fourth coordinates in the mosaic image.

The processes also include a process configured to provide the selected text result.

BRIEF DESCRIPTION OF THE DRAWINGS

The invention will be more fully understood by referring to the following Detailed Description of Specific Embodiments in conjunction with the Drawings, of which.

DETAILED DESCRIPTION

Embodiments of the present invention provide a medical device monitoring system and method that extract information from screen images from medical device controllers, with a single OCR process invocation per screen image, despite critical information appearing in different screen locations, depending on which medical device controller's screen image is processed.

Figure 1:
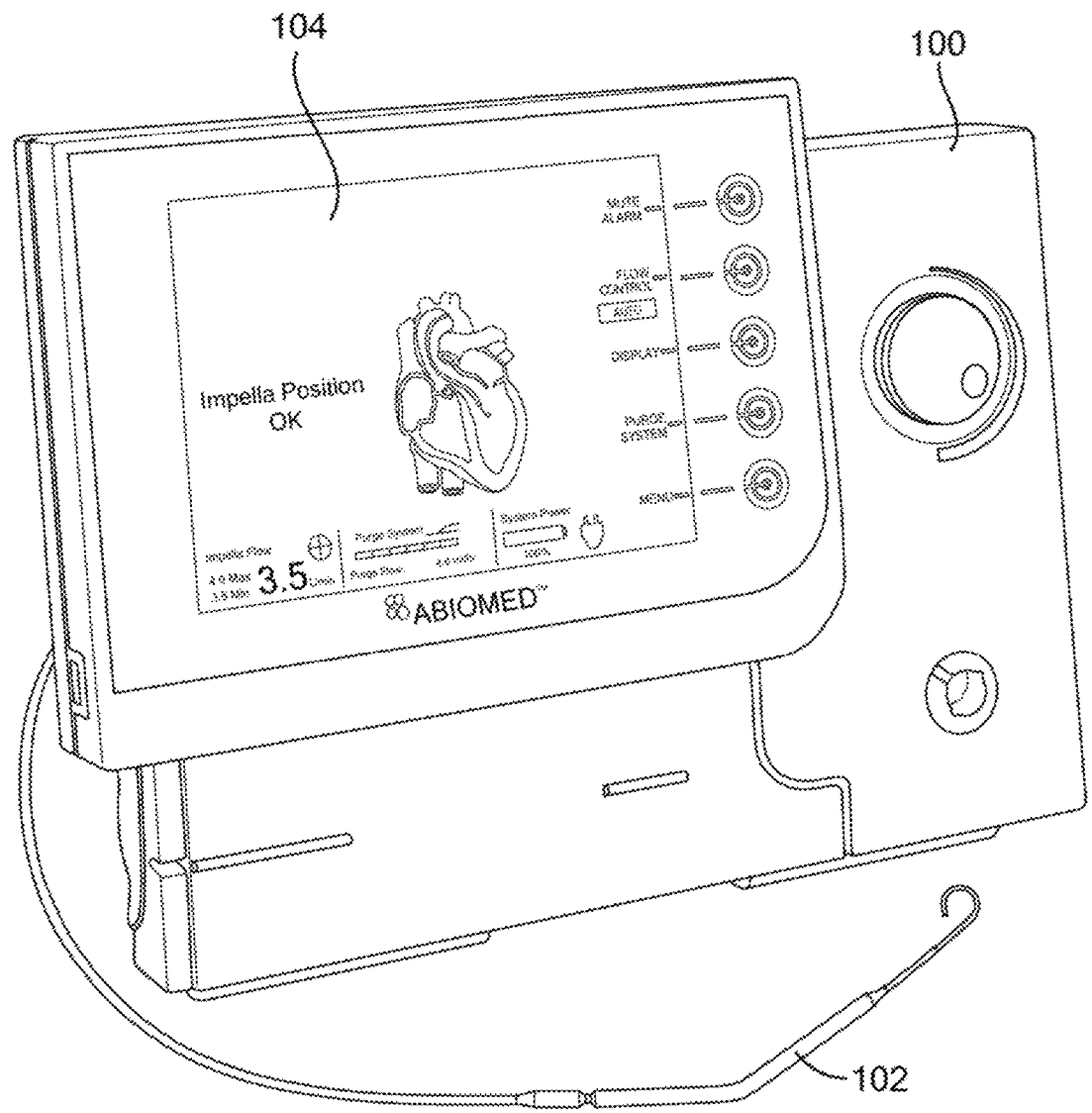
FIG. 1 is a perspective view of an exemplary convention medical device controller and an exemplary conventional medical device, in this example a heart pump, coupled to the medical device controller, according to the prior art.

FIG. 1 is a perspective view of an exemplary convention medical device controller 100 and an exemplary conventional medical device 102, in this example a heart pump, coupled to the medical device controller 100. In the example shown in FIG. 1, the medical device controller 100 is an Automated Impella Controller® from Abiomed, Inc., Danvers, MA, and the heart pump 102 is an Impella® 2.5 heart pump, also available from Abiomed, Inc., although any suitable medical device controller may be used. In some cases, the medical device and its associated medical device controller are combined. Such a combination is referred to herein simply as a medical device controller.

The medical device controller 100 includes a display screen 104, on which the medical device controller 100 displays operational data about the medical devices, such as heart signal level, battery temperature, blood flow rate and plumbing integrity. As discussed in more detail herein, the medical device controller 100 may be connected to a computer network and thereby send images of contents displayed on the screen 104 to a remote server (not shown).

Figure 2:
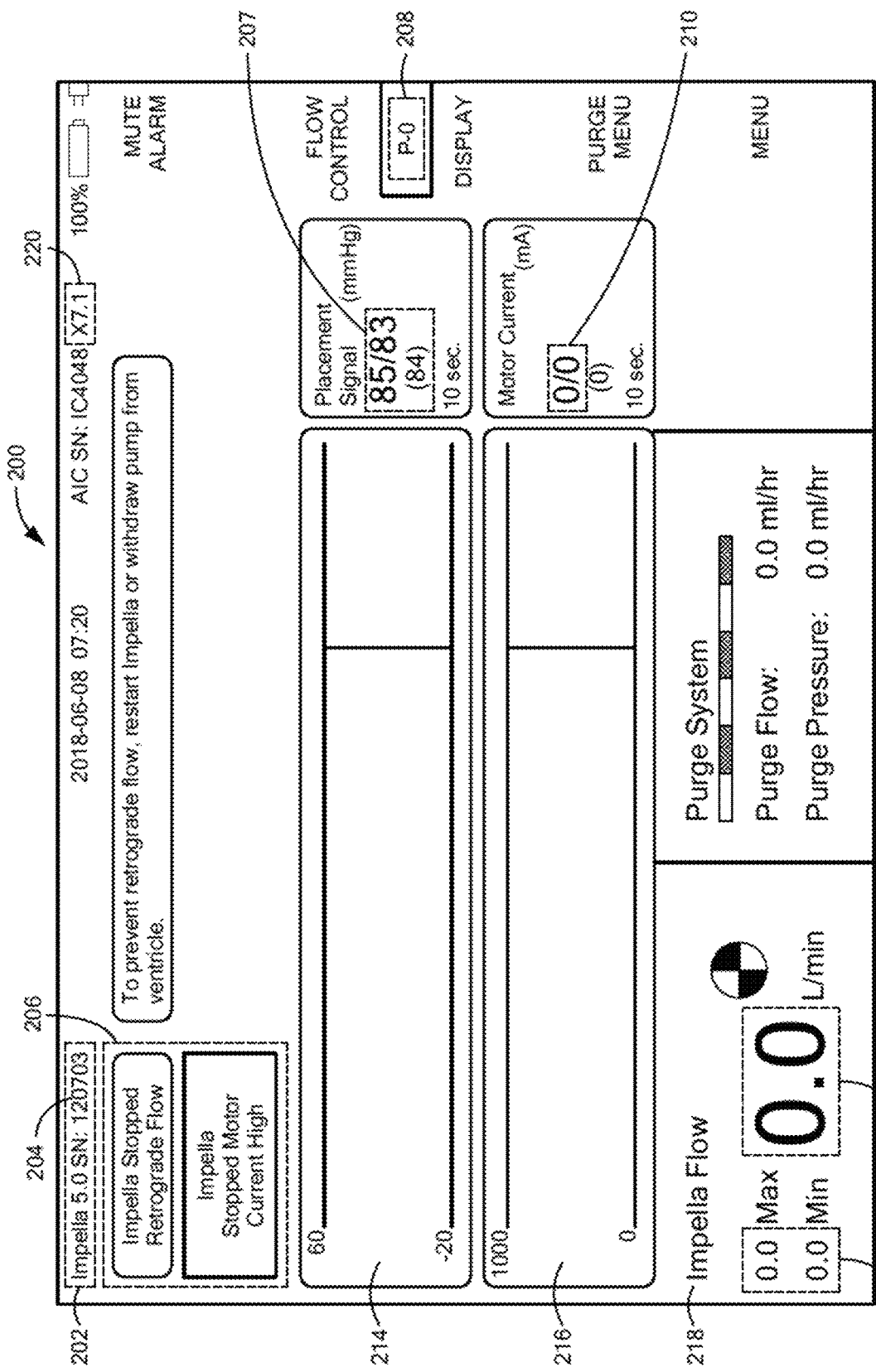
FIG. 2 shows exemplary hypothetical display screen contents that may be displayed on a screen of the medical device controller of FIG. 1, according to the prior art.

FIG. 2 shows exemplary hypothetical display screen contents 200 that may be displayed on the screen 104 of the medical device controller 100 of FIG. 1. For example, the display screen contents may include a heart pump type ("Impella 5.0") 202, a heart pump serial number ("120703") 204, one or more warning/error/informational messages 206, a placement signal 207, a present heart pump speed (performance) setting ("P-0") 208, a heart pump motor current value 210, a current blood flow rate 212 and minimum and maximum blood flow rates 213. The display screen contents 200 are typically pixelated.

Figure 3:
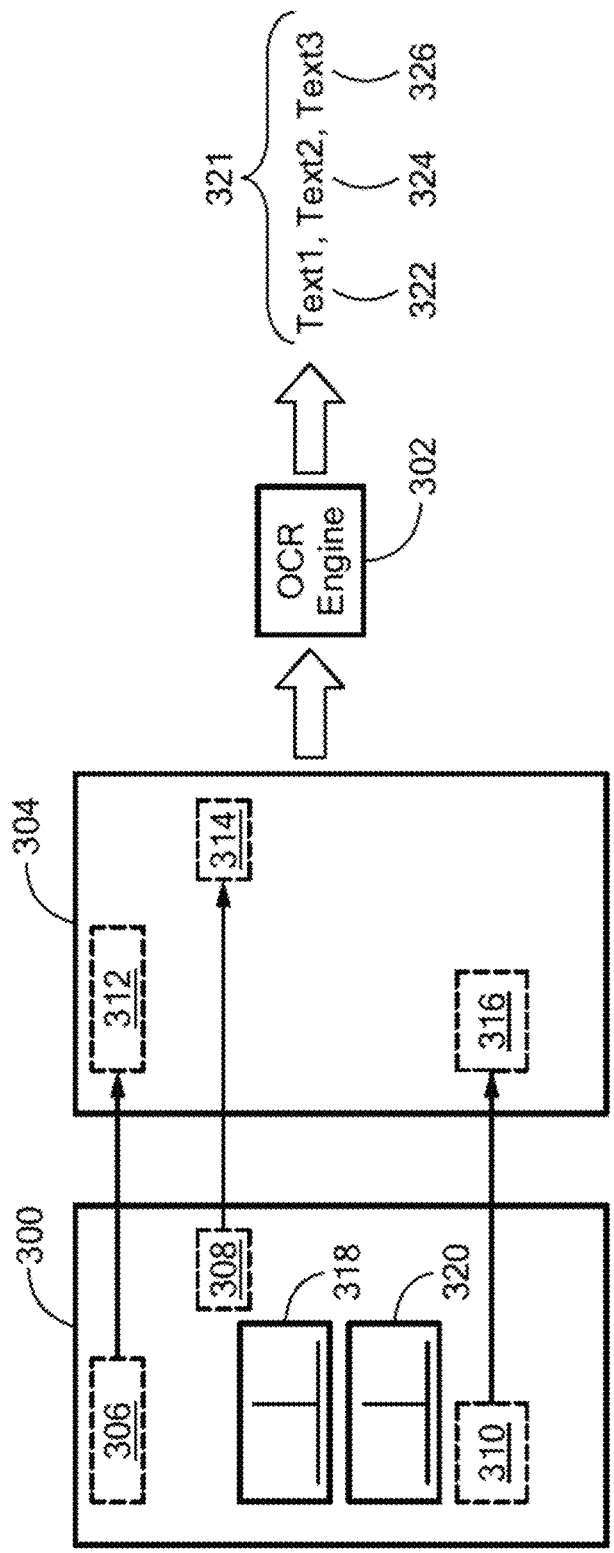
FIG. 3 schematically illustrates steps for processing a screen display image, such as the hypothetical display screen contents of FIG. 2, according to an embodiment of the present invention.

FIG. 3 schematically illustrates steps for processing a screen display image 300, such as the hypothetical display screen contents 200 of FIG. 2. Although FIG. 3 is a schematic diagram, portions of FIG. 3, such as a screen image 300, show approximate locations and sizes of certain items, such as heart pump type source region 306 and graphs 318 and 320, consistent with the exemplary hypothetical display screen contents 200 shown in FIG. 2.

As noted, to reduce OCR errors, some servers mask portions of the screen images 200, 300 that contain irrelevant text or graphics that might confuse an OCR engine 302. For example, the hypothetical display screen contents 200 (FIG. 2) includes graphs 214 and 216, as well as legends, such as "Impella Flow" 218 which, if included in an input to the OCR engine 302, might cause or contribute to OCR errors.

To avoid these errors, a mosaic image 304 is generated from only predetermined portions of the screen display image 300. The mosaic image 304 may, but need not, have the same dimensions, in pixels, as the screen display image 300. In this example, three source regions 306, 308 and 310 of the screen display image 300 are copied to respective predefined destination regions 312, 314 and 316, respectively, of the mosaic image 304. However, any number of source regions of the screen display image 300 may be copied to the mosaic image 304.

Each source region 306-310 may be identified by corresponding screen coordinates. As used herein, the term screen coordinates, or simply coordinates, means information identifying a position and size of a region of an image, i.e., an entire space where information is displayed or located within an image. The region may, but need not, be rectangular. The coordinates may, for example, include x and y pixel positions of a lower-left corner of the region, as well as height and width of the region in pixels. Other suitable units of measure, and other suitable formulations, may be used, as long as they identify position and extent of the region. Thus, different width fields have different coordinates, even if both fields start at the same x and y locations.

The destination regions 312-316 may, but need not, have the same coordinates as their respective corresponding source regions 306-310. That is, the destination regions 312-316 may, but need not, have the same starting positions and/or sizes as their respective corresponding source regions 306-310. In some embodiments, one or more of the destination regions 312-316 is larger than the respective corresponding source region 306-310.

In this case, the server may magnify the source region 312-316, so the magnified result fills the corresponding destination region 312-316. Exemplary magnifications include, but are not limited to, 1.1×, 1.5×, 2× and 3× magnification. Such magnification may decrease the likelihood of OCR error.

In some embodiments, the server changes the color of pixels as the pixels are copied from a source region 306-310 to a destination region 312-316. For example, the server may convert colored pixels to white pixels to increase contrast and, therefore, reduce OCR errors. The server may convert to white pixels whose total brightness, for example as determined by a sum of a pixel's red, blue and green values, exceeds a threshold value, and the server may convert all remaining pixels to black.

Irrelevant portions of the screen display image 300, such as graphs 318 and 320 (corresponding to graphs 214 and 216 in FIG. 2), are not copied to the mosaic image 304. The screen coordinates of the source regions 306-310 should be selected to avoid text and/or graphics that, if included, might confuse the OCR engine 302 or cause the OCR engine 302 to include spurious text in the output of the OCR engine 302. The remainder of the mosaic image 304 is left blank.

Once the mosaic image 304 has been generated, the mosaic image 304 is passed to the OCR engine 302 for conversion to text. A server may include the OCR engine 304, or the server may invoke an external OCR engine, such as Google Cloud Vision API OCR engine provided by Google (Alphabet, Inc., Mountain View, CA). The OCR engine 302 returns text results 321, represented by Text1 322, Text2 324 and Text3 326 corresponding, respectively, to destination regions 312-316. A server extracts Text1 322, Text2 324 and Text3 326 from the text results 321.

Optionally, the text results 321, or portions thereof, such as Text 1, Text2 and/or Text 3 322-326, may be validated using predefined rules, such as "pump serial number must be numeric, between five and seven digits." Such validation may prevent some OCR errors corrupting subsequent displays, etc. Also optionally, the text results 321, or portions thereof 322-326, may be cleaned up according to predefined procedures, such as "delete leading and trailing spaces in error messages." These predefined rules and procedures may be stored in a configuration file, which is described in more detail herein.

Figure 4:
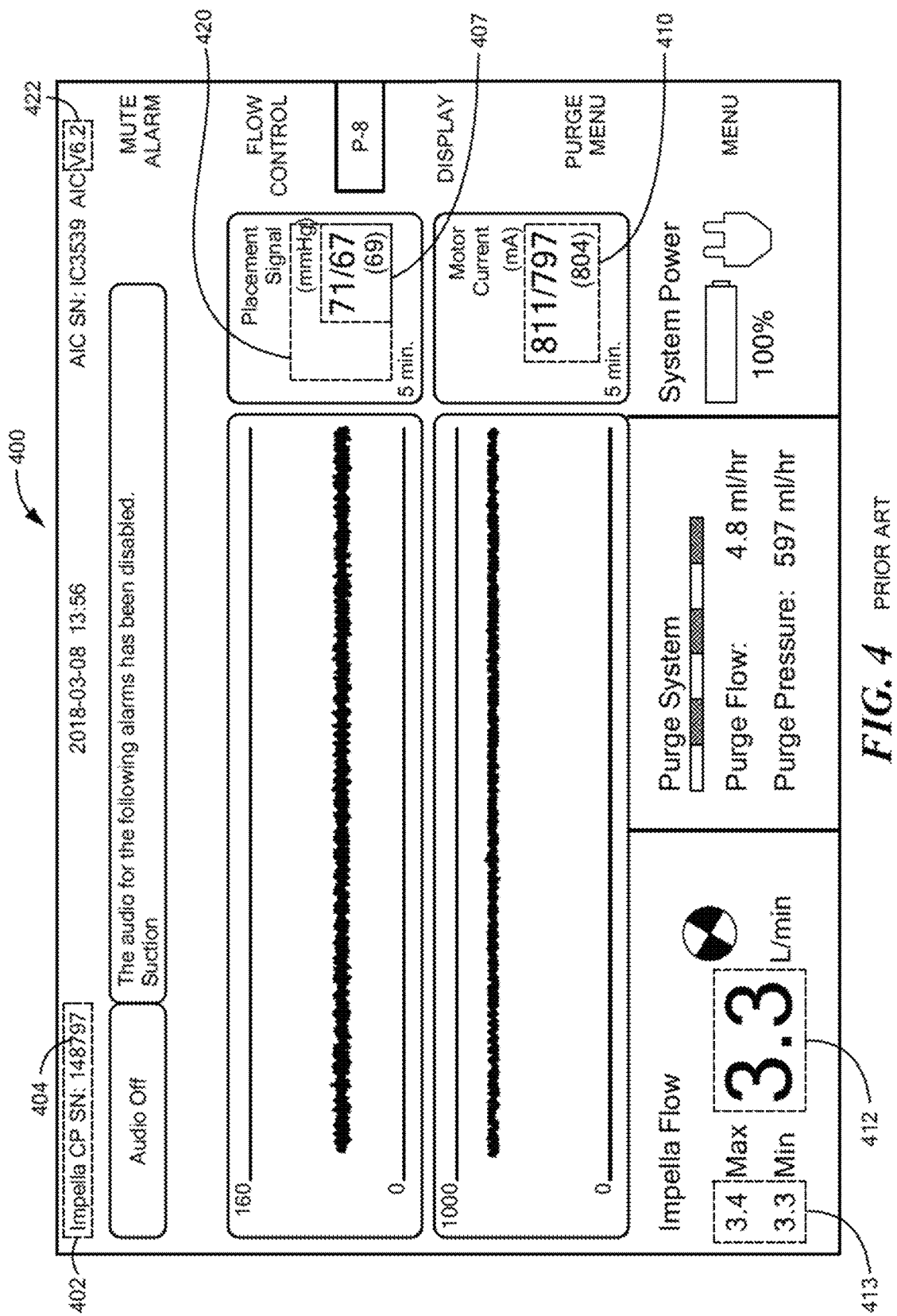
FIG. 4 shows another exemplary hypothetical display screen contents that may be displayed on a screen of another medical device controller, for example a medical device controller that executes a different version of software from the medical device controller that generated the screen contents shown in FIG. 2, according to the prior art.

As noted, different medical device controllers 100 (FIG. 1) might display the same type of information, for example blood flow rate, at different locations on their respective screens 104, for example depending on which version of software the medical device controllers execute, or depending on which type of heart pump 102 is connected to the medical device controller 100. FIG. 4 shows another exemplary hypothetical display screen contents 400 that may be displayed on the screen 104 of another medical device controller 100, for example a medical device controller 100 that executes a different version of software from the medical device controller that generated the screen contents 200 (FIG. 2), or to which a different type of heart pump 102, such an Impella® CP heart pump from Abiomed, Inc., is connected.

In the exemplary hypothetical display screen contents 400, it can be seen that the heart pump type ("Impella CP") 402 is different from the corresponding heart pump type 202 shown in the screen contents 200 (FIG. 2), indicating that a different type of heart pump is connected to the medical device controller that generated the display screen contents 400. The heart pump serial number is shown at 404. As can be seen by comparing FIGS. 4 and 2, some of the information in the display contents 400 is displayed at different respective locations from corresponding information in the display contents 200. For example, placement signal 407, motor current 410 and current, minimum and maximum blood flow rate 412 and 413 are each at screen coordinates (positions and/or sizes) from the same information 207, 210, 212 and 213, respectively, in the screen contents 200 (FIG. 2).

Clearly, this difference in screen coordinates poses problems for a single server that receives screen images from both of the medical device controllers and attempts to mask relevant portions of the screen in the manner discussed with respect to FIG. 3. Simply defining a source region that is large enough to encompass both versions of the display would fail, because such a large source region, for example source region 420 would encompass extraneous text ("mmHg") in the display contents 400.

Figure 5:
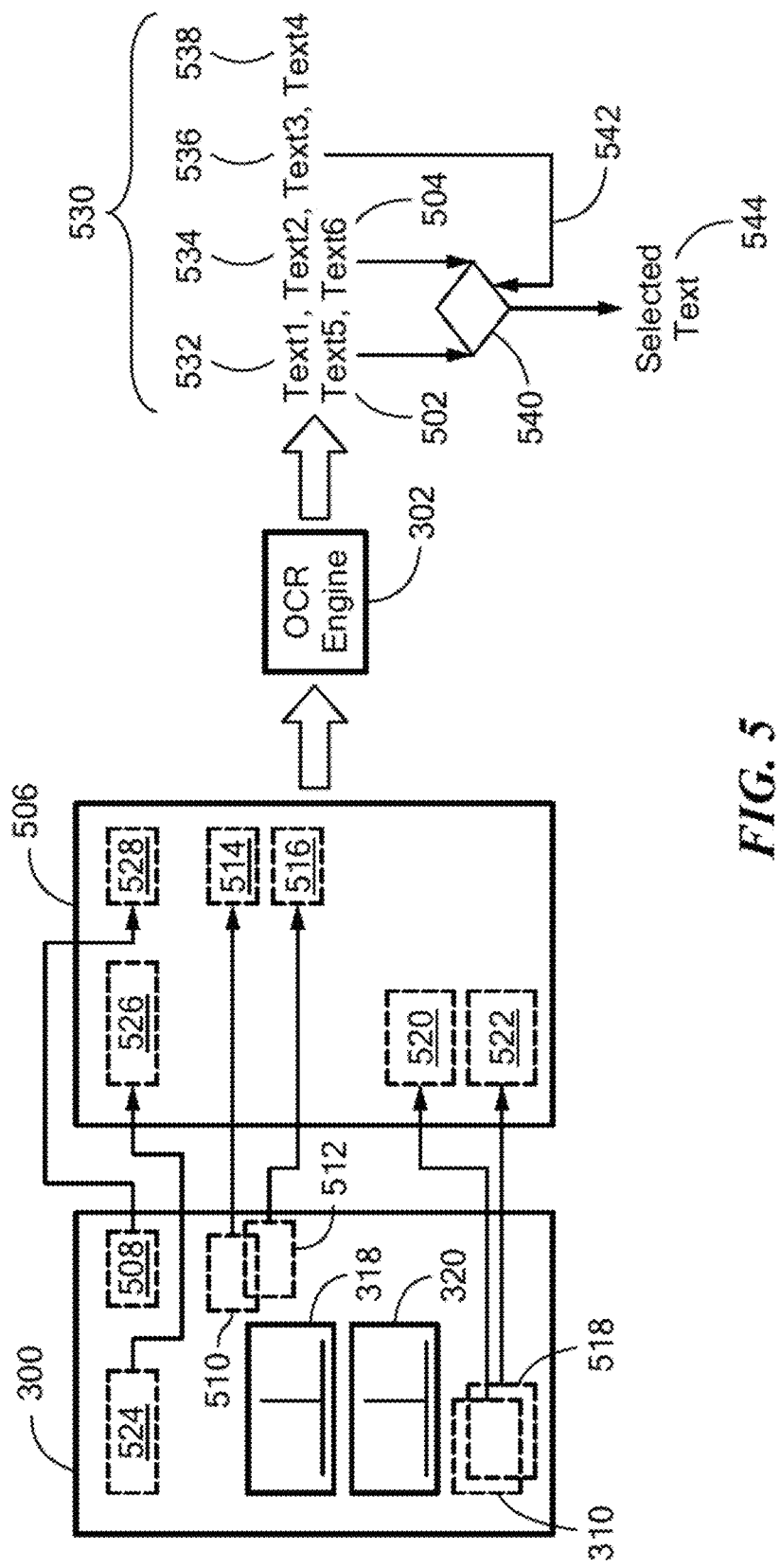
FIG. 5 schematically illustrates steps for processing a screen display image, such as the hypothetical display screen contents of FIG. 2 or the hypothetical display screen contents of FIG. 4, notwithstanding the differences between the hypothetical display screen contents of FIGS. 2 and 4, according to an embodiment of the present invention.

Embodiments of the present invention solve this problem, as schematically illustrated in FIG. 5. Although FIG. 5 is a schematic diagram, portions of FIG. 5, such as a screen image 300, show approximate locations and sizes of certain items, such as heart pump type 306 and graphs 318 and 320, consistent with the exemplary hypothetical display screen contents 200 and 400 shown in FIGS. 2 and 4. FIG. 5 schematically illustrates steps for processing the screen display image 300, such as the hypothetical display screen contents 200 of FIG. 2 or the hypothetical display screen contents 400 of FIG. 4, notwithstanding the differences between the hypothetical display screen contents 200 and 400.

Embodiments of the present invention solve the problem by making a copy of each source region that appears at different screen coordinates on respective screens 104 of different medical device controllers 100. Each of these copies is processed by an OCR engine 302, producing potentially multiple text results, for example Text5 502 and Text6 504. After the mosaic image 506 is processed by the OCR engine 302, one of the text results Text5 502 or Text6 504 is selected, based on which medical device controller 100 generated the screen image 300. Which medical device controller 100 generated the screen image may be determined, for example, by a software version number 508 displayed on the screen 104 and processed by the OCR engine 302, as described in detail next.

Continuing with the example hypothetical display screen contents 200 and 400, and as noted, the placement signal 207 (FIG. 2) appears at different screen coordinates in the display screen contents 200 from the placement signal 407 (FIG. 4) in the display screen contents 400. As shown in FIG. 5, the placement signal 207 (from FIG. 2) appears in a source region 510, whereas the placement signal 407 (from FIG. 4) appears in a source region 512. Source region 512 overlaps source region 512. Each of these source regions 510 and 512 is copied to a distinct predefined destination region 514 and 516, respectively, in the mosaic image 506. Ideally, the destination regions 514 and 516 do not overlap.

Similarly, the present blood flow rate 212 (FIG. 2) appears at different screen coordinates in the display screen contents 200 from the present blood flow rate 412 (FIG. 4) in the display screen contents 400. As shown in FIG. 5, the present blood flow rate 212 (from FIG. 2) appears in a source region 310, as it does in FIG. 3, whereas the present blood flow rate 412 (from FIG. 4) appears in a source region 518. Each of these source regions 310 and 518 is copied to a distinct destination region 520 and 522, respectively, in the mosaic image 506. Ideally, the destination regions 520 and 522 do not overlap.

Source region 310 overlaps source region 518. However, overlap of the two source regions is not required. Other text and/or graphics, proximate one or both of the source regions 310 and/or 518, may be avoided by copying the source regions 310 and 518 to the distinct destination regions 520 and 522.

Source regions that do not pose problems for the OCR engine 302 are each copied to only one respective destination region. For example, if the heart pump type 202 (FIG. 2) occupies the same screen coordinates as the heart pump type 404 (FIG. 4), a source region that encompasses the heart pump type text on the screen 104 is copied to a single destination region 526 in the mosaic image 506. Even if the heart pump type 202 (FIG. 2) does not occupy the same screen coordinates as the heart pump type 404 (FIG. 4), but a single larger source region can encompass both heart pump type fields 202 and 404, without risking OCR errors, the larger source region can be copied to a single destination region.

Similarly, if a software version number occupies the same screen coordinates in both hypothetical display screen contents 200 and 400, or a larger source region can encompass both software version numbers without risking OCR errors, the source region 508 can be copied to a single destination region 528.

Coordinates of the various source regions 310, 508, 510, 512, 518 and 524, and coordinates of the various destination regions 514, 516, 520, 522, 526 and 528, may be stored in the configuration file, rather than hard-coded, to facilitate adding and adjusting these values, for example in response to changes in software executed by the medical device controllers 100.

Once the mosaic image 504 has been generated, the mosaic image 504 is passed to the OCR engine 302 for conversion to text. The OCR engine 302 returns text results 530, represented by Text1 532, Text2 534, Text3 536, Text4 538, Text5 502 and Text6 504 corresponding, respectively, to destination regions 514, 516, 528, 526, 520 and 522, as discussed herein, with respect to FIG. 3. A server extracts Text1 532, Text2 534, . . . , Text6 504 from the text results 530.

Assuming the differences between the hypothetical display screen contents 200 and 400 are attributable to the version of software being executed by the respective medical device controllers 100 that generated the screen contents 200 and 400, a server extracts Text3 536 from the text results 530. Text3 536 contains an optical character recognition of the software version number displayed on the screen 104, for example as indicated at 220 (FIG. 2). A selector 540 selects either Text5 502 or Text6 504, depending on the value of Text3 536, i.e., the software version. For example, the selector 540 may compare Text3 536 to possible values of the software version, and then choose either Text5 502 or Text6 504, depending on which of the possible values of the software version matches the actual software version value Text3 536. Thus, the Text3 536 serves as an input 542 to the selector 540. The text chosen by the selector 540 is provided as an output 544 from the selector 540.

The selected text 544 may then be processed by another component, such as a comparator that compares the value to predetermined minimum and maximum values and raises an alarm if the present value is outside a range defined by the minimum and maximum values.

Similarly, the selector 540 selects between Text1 532 and Text2 534, which correspond to destination regions 514 and 516, respectively. Although a selection between only two choices is described in the example of FIG. 5, more than two types of medical device controllers 100 may send screen images 300. In this case, each of some of the source regions 310, 508-512, 518 and 524 may be copied to three, four or more distinct destination regions in the mosaic image 506, as needed to avoid ambiguity in optical character recognition.

In the previous example, the version number of software being executed by the medical device controller 100 is used to select between duplicated destination regions 520 and 522 and duplicated destination regions 514 and 516. However, in other cases, other information that can be extracted from the display image 300 may be used to provide the input 542 to the selector 540. For example, if appropriate, the heart pump type 202 (FIG. 2), which is encompassed by source region 524 and destination region 526, and corresponds to Text4 538, may be used as the input 542 to the selector 540.

Preferably, the text or other indicator from the display image 300 that is used to derive the input 542 to the selector 540 is present at the same screen coordinates on each screen 104 of the various medical device controllers 100. However, as with the software version number, the text or other indicator may be located at different coordinates on screens 104 of different medical device controllers 100, as exemplified by the hypothetical display screen contents 200 (FIG. 2) and 400 (FIG. 4). In some cases, the source region used to drive the selector 540, for example source region 508, need not encompass all the possible screen locations where the text or other indicator may be displayed, as long as the selector 540 receives sufficient input 542 to make a choice.

For example, if the source region 508 encompasses the software version 220 (FIG. 2) in the hypothetical display screen contents 200, but not the software version 422 (FIG. 4) in the hypothetical display screen contents 400, the selector 540 may choose Text5 502 if Text3 536 contains "X7.1" (the software version number displayed in hypothetical display screen contents 200), and the selector 540 may choose Text6 504 if Text3 536 does not contain "X7.1" In other words, the selector 540 may default to a predetermined choice, such as Text3 536, if the input 542 does not match any predetermined value.

Although in this example only destination region 528 is used to drive the selector 540, the input 542 to the selector 540 may include text from any combination of destination regions 514, 516, 520, 522, 526 and 528. For example, if the software version number is a greater than a particular value, and the heart pump is a particular model, then the OCR value derived from one destination region may be used, whereas if the software version number is less than or equal to the particular value, the OCR value derived from a different destination region may be used. Furthermore, the decision process carried out by the selector 540 may involve several steps. For example, if the medical device is a particular heart pump model, then the software version number may be used to make the selection, but if the medical device is another particular heart pump model, then the heart pump serial number may be used to make the selection.

Examples of text or other indicator from the display image 300 that may be used to derive the input 542 to the selector 540 include: software version, hardware version, heart pump model identifier, heart pump serial number, an indication of an optional feature or component present or installed in the heart pump or the medical device controller, an indication of an option selected by a user or administrator (for example, to customize the way information is displayed on the screen 104), and combinations thereof.

Figure 6:
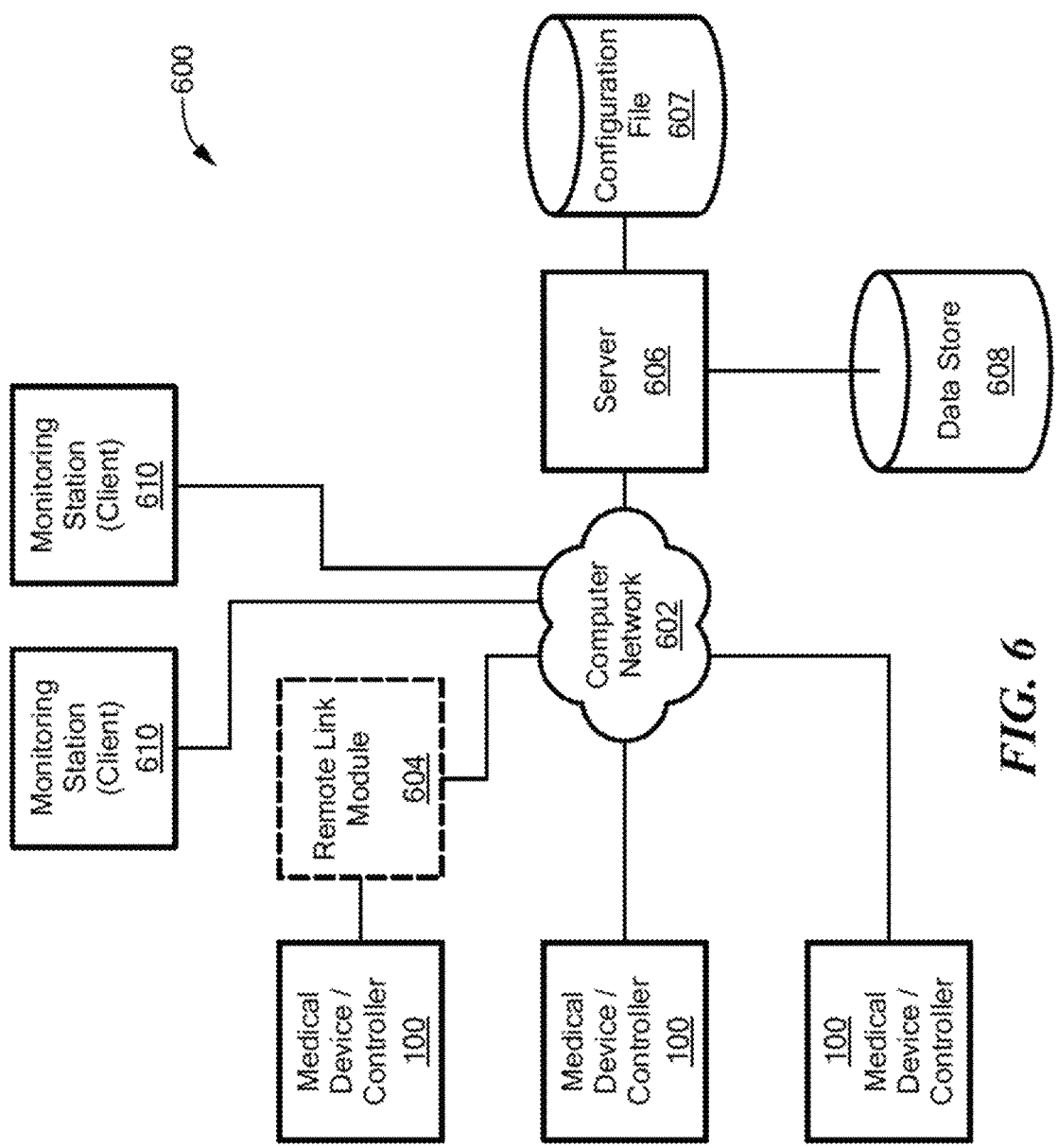
FIG. 6 is a schematic block diagram of major components of a medical device monitoring system for collecting, storing and retrieving operational data from and about a plurality of medical device controllers, including a server that performs the processing steps shown in FIG. 5, according to an embodiment of the present invention.

FIG. 6 is a schematic block diagram of major components of a medical device monitoring system 600 for collecting, storing and retrieving operational data from and about a plurality of medical device controllers 100. For simplicity, only medical device controllers 100, and not separate medical devices, are shown in FIG. 6. Although three medical device controllers 100 are shown, other numbers of medical device controllers 100 may be used. Each medical device controller 100 is connectable to a computer network 602, optionally via a remote link module 604. Each medical device controller 100 is configured to automatically repeatedly capture status information about the medical device connected thereto and display the status information on a display screen 104 (FIG. 1). As noted, FIGS. 2 and 4 show respective hypothetical display screen contents 200 and 400 that may be displayed on the screen 104 of any given medical device controller 100.

A server 606 is configured to automatically periodically or occasionally request and receive an image of the contents displayed on the screen 104 of each medical device controller 100, typically about every 20 second. The request and the image are sent via the computer network 602. The image may be sent in one or more messages encoded as a video frame or a sequence of video frames. The video frame(s) may, for example, contain pixelated copies of images displayed on display screens 104 of the medical device controllers 100.

The server 606 is configured to process the received frames (images), as described with respect to FIGS. 2-5. As noted, validation rules, clean up procedures and the coordinates of the various source regions 310, 508, 510, 512, 518 and 524, and coordinates of the various destination regions 514, 516, 520, 522, 526 and 528, may be stored in a configuration file 607. The server 606 may communicate with an external OCR engine (not shown) via the computer network 602. The server 606 may then use the recognized, and in some cases selected, text to automatically ascertain serial numbers or other identifiers of the medical device controllers 100, operating parameters of the medical device controllers 100, whether an alarm has been raised by one of the medical device controllers 100, etc.

A data store 608 is configured to store one or more media files, and in particular frames (images), such as MP4 video or other suitable types of media files, and the server 606 is configured to automatically store received frames (images) in the data store 608. The data store 608 records the screen images received by the server 606 for later playback, such as in response to requests from one of several monitoring stations 610. The data store 608 is configured to provide a requested portion of the stored media file in response to a provision request. The data store 608 thereby supports playback of the medical device controller 100 status information. For example, the data store 608 may provide one or more frames (images) of video stored in the media file, for display to a user.

The server 606 may also be configured to provide status information about one or more of the medical device controllers 100 to ones of the monitoring stations 610, based on images received by the server 606 in real time and/or based on historical information held in the data store 608.

Figure 7:
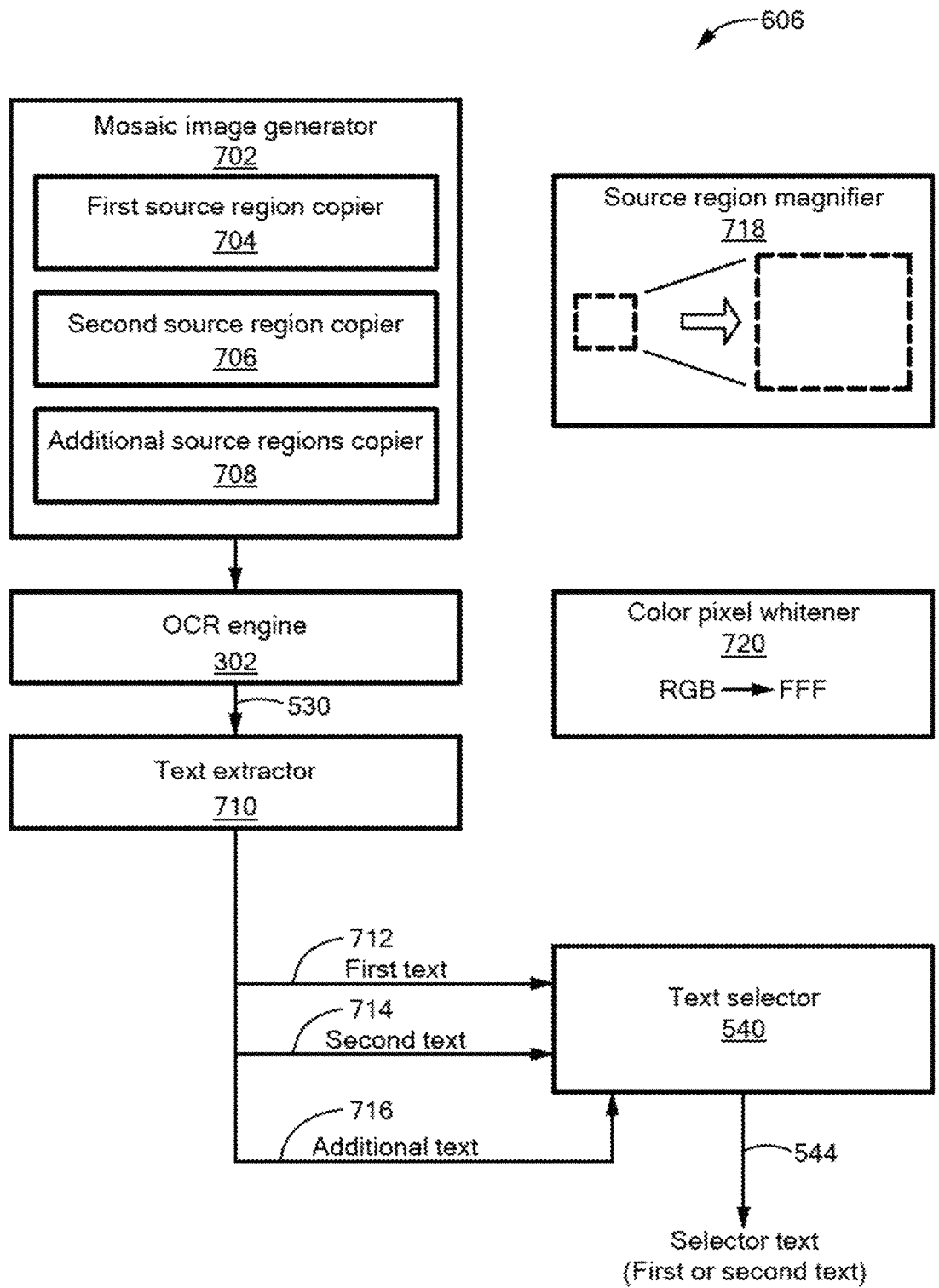
FIG. 7 is a schematic block diagram of a server of FIG. 6, according to an embodiment of the present invention.

FIG. 7 is a schematic block diagram of the server 606 of FIG. 6. The server 606 includes a mosaic image generator 700 configured to generate the mosaic image 506 (FIG. 5). The mosaic image generator 700 includes a first source region copier 704, a second source region copier 706 and an additional source regions copier 708. Although the first, second and additional source regions copiers 704-708 are shown as separate components, some or all of these copiers 704-708 may share code or other components.

For each piece of information that appears at different screen coordinates in the hypothetical display screen contents 200 and 400 and that might cause an OCR error if extracted from the screen image 300 (FIG. 5) as a single source region, the first source region copier is configured to copy one of the source regions, encompassed by first screen coordinates, in the screen image 300 to a predefined destination region at third coordinates in the mosaic image 506, as discussed herein. Similarly, the second source region copier is configured to copy the other source region, encompassed by second screen coordinates, in the screen image 300 to a predefined destination region at fourth coordinates, different from the third coordinates, in the mosaic image 506, as discussed herein.

Examples of such source regions include the present blood flow rate source regions 310 and 518, which are copied to destination regions 520 and 522, respectively, and the placement signal source regions 510 and 512, which are copied to destination regions 514 and 516, respectively.

The additional source regions copier 708 is configured to copy source regions of the screen image 300 that would not cause OCR errors to the mosaic image 506, as discussed herein. The additional source regions copier 708 is configured to copy a plurality of additional source regions of the screen image 300 to respective additional predefined destination regions in the mosaic image 506. Examples of such source regions include the pump type source region 524 and the software version number source region 508, which are copied to destination regions 526 and 528, respectively.

As noted, the server 606 may include an OCR engine, or the server 606 may make service calls to an external OCR engine. Both these embodiments are represented by the OCR engine 302 in FIGS. 5 and 7. After the mosaic image 506 is generated, the OCR engine parses the mosaic image 506 and returns text results 530.

A text extractor 710 is configured to extract a first text result 712 from the text results 530. The first text result 712 corresponds to the third coordinates in the mosaic image 506. For example, the first text result 712 may correspond to the present blood flow rate source region 310 and the corresponding destination region 520.

The text extractor 710 is also configured to extract a second text result 714 from the text results 530. The second text result 714 corresponds to the fourth coordinates in the mosaic image 506. For example, the second text result 714 may correspond to the present blood flow rate source region 518 and the corresponding destination region 522.

The text extractor 710 is further configured to extract at least one additional text result 716 from the text results 530. The at least one additional text result 716 corresponds to the at least one additional predefined destination regions in the mosaic image 506. For example, the at least one additional text result 716 may correspond to the pump type source region 524, which corresponds to the destination region 526, and/or the at least one additional text result 716 may correspond to the software version number source region 508, which corresponds to the destination region 528.

A text selector 540 chooses either the first or second text results 712 or 714, based on the additional text result 716. For example, the text selector 540 may choose the first or second text result 712 or 714, based on the software version, or based on the type of heart pump. The text selector 540 provides the choses (selected) text 544.

As noted, the server 606 may magnify certain source regions. Optionally, a source region magnifier 718 is configured to magnify a first source region so as to fill a predefined destination region at the third coordinates.

As noted, the server 606 may convert colored pixels to white pixels. Optionally, a color pixel whitener 720 is configured to convert each colored pixel of the first source region to a white pixel in the predefined destination region at the third coordinates.

Figure 8:
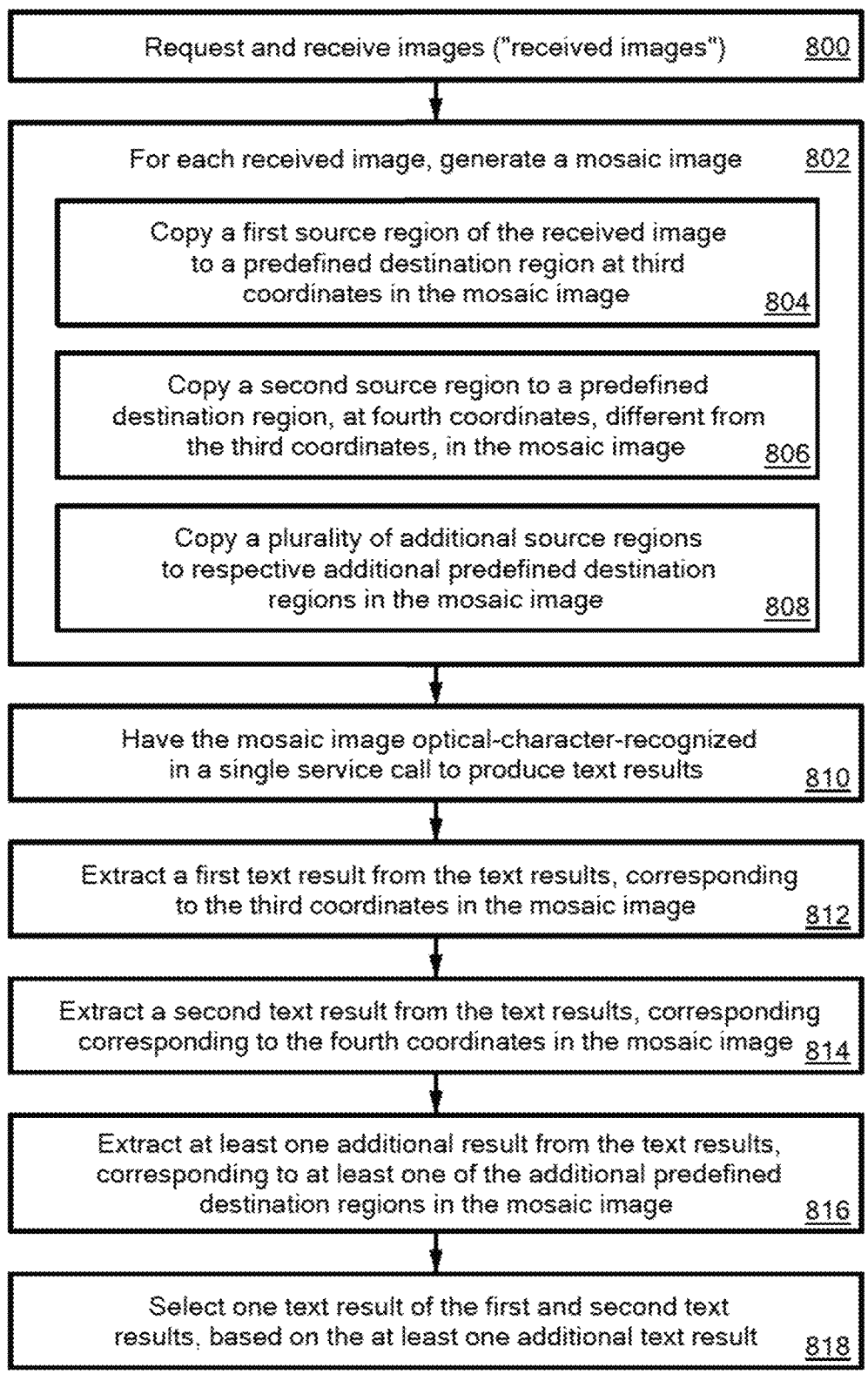
FIG. 8 is a flowchart schematically illustrating a method of monitoring a medical device, such as a method performed by the server of FIGS. 6 and 7, according to an embodiment of the present invention.

FIG. 8 is a schematic flowchart illustrating operations of a method of monitoring a medical device. The method may be performed by the server 606 (FIGS. 6 and 7), and the server 606 may be configured to perform the method. At operation 800, the method includes requesting and receiving images ("received images"). The received images are requested and received via a computer network. The received images are requested and received from each medical device controller of a plurality of medical device controllers. Each received image includes contents displayed on a screen of the medical device controller. The plurality of medical device controllers includes a plurality of first medical device controllers, each configured to display information of a first type at first screen coordinates, and a plurality of second medical device controllers, each configured to display information of the first type at second screen coordinates, different from the first screen coordinates.

At 802, for each received image, a mosaic image is generated. Generating each mosaic image includes: 804 coping a first source region, which encompasses the first screen coordinates of the received image, to a predefined destination region at third coordinates in the mosaic image; 806 copying a second source region, which encompasses the second screen coordinates of the received image, to a predefined destination region at fourth coordinates, different from the third coordinates, in the mosaic image; and 808 copying a plurality of additional source regions of the received image to respective additional predefined destination regions in the mosaic image.

After generating the mosaic image, at 810, the mosaic image is optical-character-recognized in a single service call to produce text results.

At 812, a first text result is extracted from the text results. The first text result corresponds to the third coordinates in the mosaic image. At 814, a second text result is extracted from the text results. The second text result corresponds to the fourth coordinates in the mosaic image. At 816, at least one additional text result is extracted from the text results. The at least one additional text result corresponds to at least one of the additional predefined destination regions in the mosaic image.

At 818, one text result of the first and second text results is selected, based on the at least one additional text result.

Figure 9:
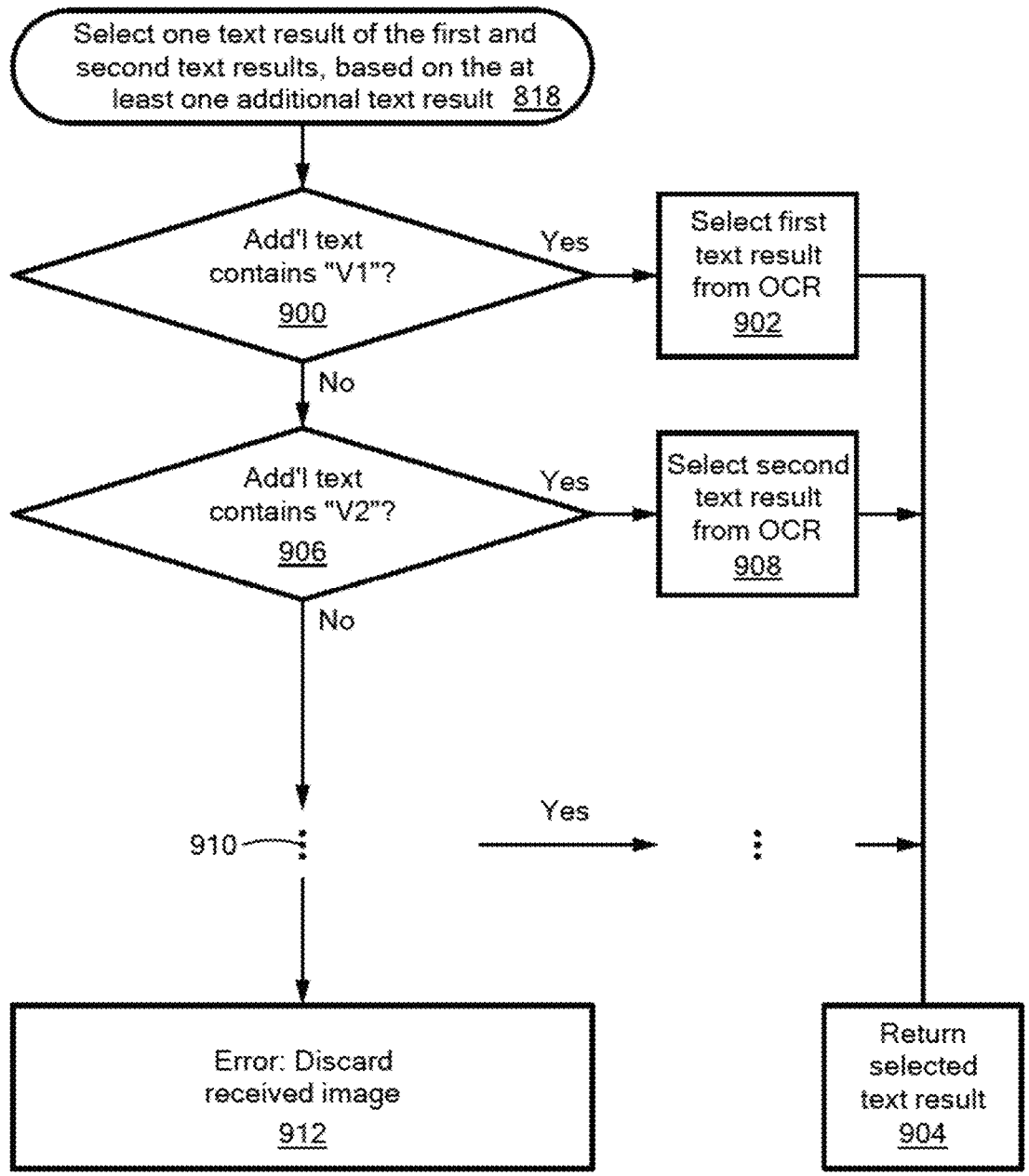
FIG. 9 is flowchart schematically illustrating details of an operation (selecting one text result, based on an additional text result) of the flowchart in FIG. 8, according to an embodiment of the present invention.

FIG. 9 is a flowchart schematically illustrating operation 818 (FIG. 8), selecting one text result of the first and second text results, based on the at least one additional text result, assuming that the selection is based on version number, and possible version numbers are "V1," "V2," etc. Of course, the flowchart may be modified accordingly, if the selection criteria are different. At 900, the additional text 716 (FIG. 7) is compared to "V 1." If the additional text 716 contains (alternatively, equals) "V1," control passes to 902, where the first text result 712 from the OCR engine 302 is selected. Control then passes to 904, where the selected text is returned as the text result 544.

On the other hand, if at operation 900 the at least one additional text result does not contain (alternatively, equal) "V1," then control passes to 906, where the additional text 716 is compared to "V2." If the additional text 716 contains (alternatively, equals) "V2," control passes to 908, where the second text result 714 from the OCR engine 302 is selected. Control then passes to 904, where the selected text is returned as the text result 544.

Additional test may be made, as indicated by ellipses 910, to compare the additional text 716 to other predetermined values. If, however, none of the comparisons 900, 906, etc. find a match, control passes to 912, which discards the received image 300 (FIG. 5).

Figure 10:
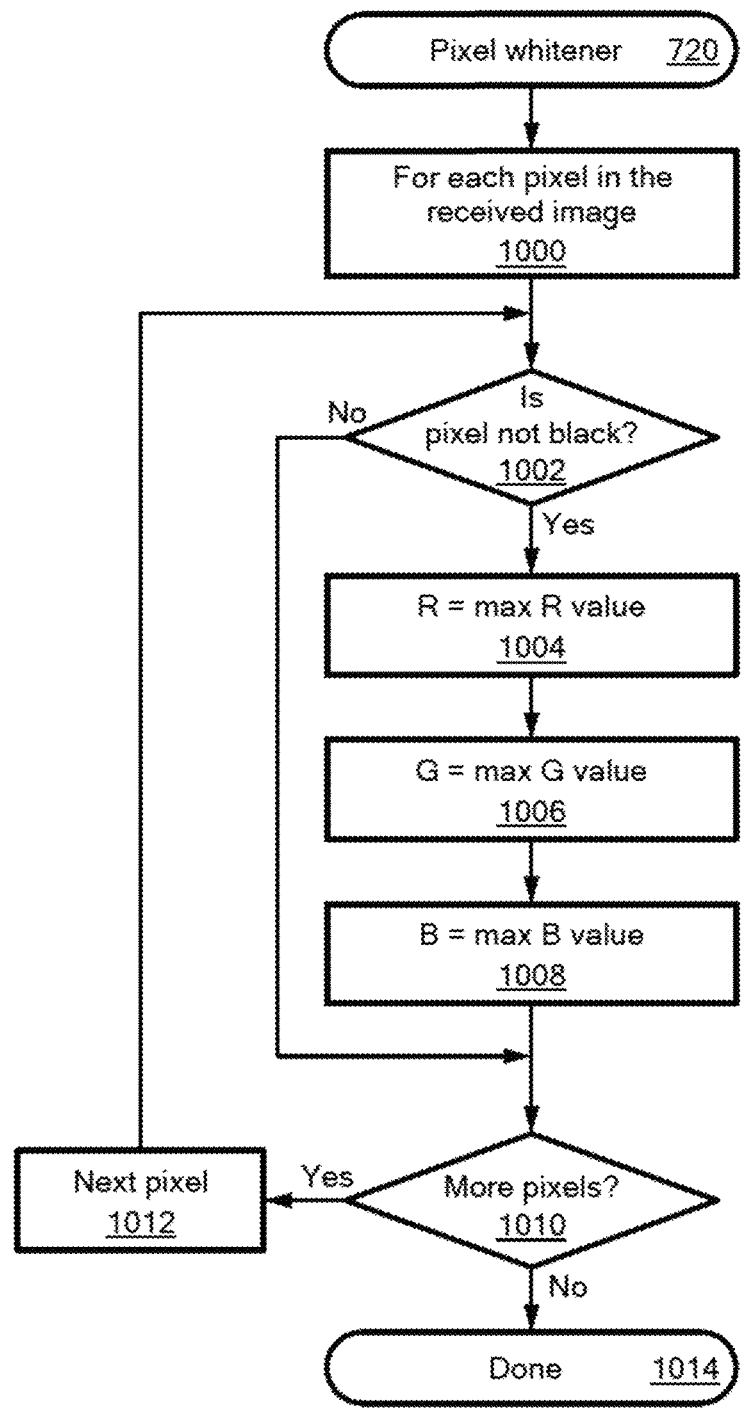
FIG. 10 is a flowchart schematically illustrating operations performed by an optional color pixel whitener of the server of FIGS. 6 and 7, according to an embodiment of the present invention.

FIG. 10 is a flowchart schematically illustrating operations performed by the optional color pixel whitener 720 (FIG. 7). At 1000, a loop is initiated. The loop is traversed once for each pixel (referred to as the "current pixel"). At 1002, if the current pixel is not black (alternatively, a sum of the pixel's red, green and blue values exceeds a predetermined threshold value), control passes to 1004, where the pixel's red value is set to its maximum possible value, such as FF (hexadecimal). From there, control passes successively to 1006 and 1008, where, respectively, the pixel's green value is set to its maximum possible value, and the pixel's blue value is set to its maximum possible value. Control then passes to 1010.

On the other hand, if the current pixels is found at 1002 to be black (alternatively, a sum of the pixel's red, green and blue values is below the predetermined threshold value), control passes to 1010, where a check is made to determine if there are more pixels in the image to process. If there is at least one more pixel to process, control passes to 1012, where the current pixel is advanced to the next pixel, and then the loop returns control to 1002. On the other hand, if all the pixels have been processed, control passes from 1010 to 1014.

While the invention is described through the above-described exemplary embodiments, modifications to, and variations of, the illustrated embodiments may be made without departing from the inventive concepts disclosed herein. For example, although specific parameter values, such as display screen field names (for example, heart pump type, placement signal, blood flow rate, software version number and heart pump serial number), may be recited in relation to disclosed embodiments, within the scope of the invention, the values of all parameters may vary over wide ranges to suit different applications. For example, fields other than software version number and/or heart pump type may be used to discriminate between screen images generated by different medical device controllers.

As used herein, including in the claims, the term "and/or," used in connection with a list of items, means one or more of the items in the list, i.e., at least one of the items in the list, but not necessarily all the items in the list. As used herein, including in the claims, the term "or," used in connection with a list of items, means one or more of the items in the list, i.e., at least one of the items in the list, but not necessarily all the items in the list. "Or" does not mean "exclusive or."

Although aspects of embodiments may be described with reference to flowcharts and/or block diagrams, functions, operations, decisions, etc. of all or a portion of each block, or a combination of blocks, may be combined, separated into separate operations or performed in other orders. References to a "module," "operation," "step" and similar terms are for convenience and not intended to limit their implementation. All or a portion of each block, module, operation, step or combination thereof may be implemented as computer program instructions (such as software), hardware (such as combinatorial logic, Application Specific Integrated Circuits (ASICs), Field-Programmable Gate Arrays (FPGAs), processor or other hardware), firmware or combinations thereof.

The server 606, or portions thereof, may be implemented by one or more processors executing, or controlled by, instructions stored in a memory. Each processor may be a general purpose processor, such as a central processing unit (CPU), a graphic processing unit (GPU), digital signal processor (DSP), a special purpose processor, etc., as appropriate, or combination thereof.

The memory may be random access memory (RAM), read-only memory (ROM), flash memory or any other memory, or combination thereof, suitable for storing control software or other instructions and data. Instructions defining the functions of the present invention may be delivered to a processor in many forms, including, but not limited to, information permanently stored on tangible non-transitory non-writable storage media (e.g., read-only memory devices within a computer, such as ROM, or devices readable by a computer I/O attachment, such as CD-ROM or DVD disks), information alterably stored on tangible non-transitory writable storage media (e.g., floppy disks, removable flash memory and hard drives) or information conveyed to a computer through a communication medium, including wired or wireless computer networks. Moreover, while embodiments may be described in connection with various illustrative data structures, systems may be embodied using a variety of data structures.

Disclosed aspects, or portions thereof, may be combined in ways not listed above and/or not explicitly claimed. In addition, embodiments disclosed herein may be suitably practiced, absent any element that is not specifically disclosed herein. Accordingly, the invention should not be viewed as being limited to the disclosed embodiments.

As used herein, numerical terms, such as "first," "second" and "third," are used to distinguish respective source regions and destination regions from one another and are not intended to indicate any particular order or total number of source or destination regions in any particular embodiment. Thus, for example, a given embodiment may include only a second destination region and a third destination region.

The invention claimed is:

1. A medical device monitoring system, comprising:
a server configured to automatically:
request and receive, via a computer network, from a medical device controller, an image of contents displayed on a screen of the medical device controller;
generate a mosaic image, wherein the server is configured to: (a) copy a first source region, which encompasses first screen coordinates of the received image, to a predefined destination region at fourth coordinates in the mosaic image, (b) copy a second source region, which encompasses second screen coordinates of the received image, to a predefined destination region at fifth coordinates, different from the fourth coordinates, in the mosaic image, and (c) copy a third source region, which encompasses third screen coordinates of the received image, to a predefined destination region at sixth coordinates, different from the fourth and fifth coordinates, in the mosaic image;
after the mosaic image is generated, have the mosaic image optical-character-recognized to produce text results, wherein the text results comprise (a) a first text result corresponding to the fourth coordinates in the mosaic image, (b) a second text result corresponding to the fifth coordinates in the mosaic image, and (c) a selector text result corresponding to the sixth coordinates in the mosaic image; and
select one of the first text result or the second text result based on the selector text result.

2. A medical device monitoring system according to claim 1, wherein the selector text comprises a version number of software executed by the medical device controller.

3. A medical device monitoring system according to claim 1, wherein the selector text comprises an identifier of a medical device coupled to the medical device controller.

4. A medical device monitoring system according to claim 3, wherein the identifier of the medical device comprises a serial number or a type code.

5. A medical device monitoring system according to claim 1, wherein the selector text comprises an identifier of an optional feature installed on the medical device controller.

6. A medical device monitoring system according to claim 1, wherein the predefined destination region at the fourth coordinates in the mosaic image is larger than the first source region, and wherein to copy the first source region to the predefined destination region at the fourth coordinates, the server is configured to magnify the first source region so as to fill the predefined destination region at the fourth coordinates.

7. A medical device monitoring system according to claim 1, wherein to copy the first source region to the predefined destination region at the fourth coordinates, the server is configured to convert at least one non-black pixel of the first source region to a white pixel in the predefined destination region at the fourth coordinates.

8. A medical device monitoring system according to claim 1, wherein to copy the first source region to the predefined destination region at the fourth coordinates, the server is configured to convert each non-black pixel of the first source region to a white pixel in the predefined destination region at the fourth coordinates.

9. A medical device monitoring system according to claim 8, wherein to copy the second source region to the predefined destination region at the fifth coordinates, the server is configured to convert each non-black pixel of the second source region to a white pixel in the predefined destination region at the fifth coordinates.

10. A medical device monitoring system according to claim 8, wherein to copy the third source region to the predefined destination region at the sixth coordinates, the server is configured to convert each non-black pixel of the third source region to a white pixel in the predefined destination region at the sixth coordinates.

11. A medical device monitoring system according to claim 1, wherein the first source region overlaps with the second source region of the received image.

12. A medical device monitoring system according to claim 11, wherein the predefined destination region at the fourth coordinates in the mosaic image does not overlap with the predefined destination region at the fifth coordinates in the mosaic image.

13. A method of monitoring a medical device, the method comprising:
   requesting and receiving, via a computer network, from a medical device controller, an image of contents displayed on a screen of the medical device controller;
   generating a mosaic image, wherein the generation of the mosaic image comprises:
      (a) copying a first source region, which encompasses first screen coordinates of the received image, to a predefined destination region at fourth coordinates in the mosaic image;
      (b) copying a second source region, which encompasses second screen coordinates of the received image, to a predefined destination region at fifth coordinates, different from the fourth coordinates, in the mosaic image; and
      (c) copying a third source region, which encompasses third screen coordinates of the received image, to a predefined destination region at sixth coordinates, different from the fourth and fifth coordinates, in the mosaic image;
   after generating the mosaic image, having the mosaic image optical-character-recognized to produce text results, wherein the text results comprise (a) a first text result corresponding to the fourth coordinates in the mosaic image, (b) a second text result corresponding to the fifth coordinates in the mosaic image, and (c) a selector text result corresponding to the sixth coordinates in the mosaic image; and
   selecting one of the first text result or the second text result based on the selector text result.

14. A method according to claim 13, wherein the selector text comprises a version number of software executed by the medical device controller.

15. A method according to claim 13, wherein the selector text comprises an identifier of a medical device coupled to the medical device controller.

16. A method according to claim 15, wherein the identifier of the medical device comprises a serial number or a type code.

17. A method according to claim 13, wherein the selector text comprises an identifier of an optional feature installed on the medical device controller.

18. A method according to claim 13, wherein the predefined destination region at the fourth coordinates in the mosaic image is larger than the first source region, and wherein copying the first source region to the predefined destination region at the fourth coordinates comprises magnifying the first source region so as to fill the predefined destination region at the fourth coordinates.

19. A method according to claim 13, wherein copying the first source region to the predefined destination region at the fourth coordinates comprises converting at least one non-black pixel of the first source region to a white pixel in the predefined destination region at the fourth coordinates.

20. A non-transitory computer-readable medium encoded with instructions that, when executed by a processor, establish processes for performing a computer-implemented method of monitoring a medical device, the processes comprising:
   a process configured to request and receive, via a computer network, from a medical device controller, an image of contents displayed on a screen of the medical device controller;
   a process configured to generate a mosaic image, wherein the generation of the mosaic image comprises:
      (a) copying a first source region, which encompasses first screen coordinates of the received image, to a predefined destination region at fourth coordinates in the mosaic image;
      (b) copying a second source region, which encompasses second screen coordinates of the received image, to a predefined destination region at fifth coordinates, different from the fourth coordinates, in the mosaic image; and
      (c) copying a third source region, which encompasses third screen coordinates of the received image, to a predefined destination region at sixth coordinates, different from the fourth and fifth coordinates, in the mosaic image;
   a process configured to, after generating the mosaic image, have the mosaic image optical-character-recognized to produce text results, wherein the text results comprise (a) a first text result corresponding to the fourth coordinates in the mosaic image, (b) a second text result corresponding to the fifth coordinates in the mosaic image, and (c) a selector text result corresponding to the sixth coordinates in the mosaic image; and
   a process configured to select one of the first text result or the second text result based on the selector text result.

* * * * *